(12) United States Patent
Schatkowski et al.

(10) Patent No.: US 7,019,181 B2
(45) Date of Patent: Mar. 28, 2006

(54) METHOD FOR THE PREPARATION OF TRIMETHYLCYCLOHEXYL-ALKAN-3-OLS CONTAINING A HIGH PROPORTION OF TRANS ISOMERS

(75) Inventors: Dietmar Schatkowski, Stadtoldendorf (DE); Wilhelm Pickenhagen, Höxter (DE); Hartmut Struwe, Stahle (DE); Johannes Panten, Lüchtringen (DE); Klaus Schäfer, Bevern (DE)

(73) Assignee: Symrise GmbH & Co. KG, (DE)

( * ) Notice: Subject to any disclaimer, the term of this patent is extended or adjusted under 35 U.S.C. 154(b) by 0 days.

(21) Appl. No.: 10/666,777

(22) Filed: Sep. 18, 2003

(65) Prior Publication Data

US 2004/0059163 A1    Mar. 25, 2004

(30) Foreign Application Priority Data

Sep. 19, 2002    (DE) ................ 102 43 466

(51) Int. Cl.
*C07C 35/08*    (2006.01)
(52) U.S. Cl. ........................................ 568/822; 512/22
(58) Field of Classification Search ................ 568/834, 568/822; 512/22
See application file for complete search history.

(56) References Cited

U.S. PATENT DOCUMENTS

| | | | | |
|---|---|---|---|---|
| 4,246,292 A | * | 1/1981 | Konst et al. ................ | 426/538 |
| 4,252,986 A | * | 2/1981 | Klein et al. ................. | 568/822 |
| 4,588,849 A | * | 5/1986 | Schulte-Elte ................ | 568/834 |
| 4,623,750 A | * | 11/1986 | Schulte-Elte et al. ....... | 568/822 |
| 4,711,875 A | * | 12/1987 | Schulte-Elte et al. ......... | 512/1 |
| 5,250,512 A | * | 10/1993 | Ohmoto et al. ............... | 512/22 |
| 2002/0082457 A1 | | 6/2002 | Kuhn et al. | |

FOREIGN PATENT DOCUMENTS

| | | | |
|---|---|---|---|
| DE | 24 55 761 A | | 11/1974 |
| DE | 100 62 771 A | | 11/2002 |
| SU | 1082780 A | * | 3/1984 |

OTHER PUBLICATIONS

Chemical Abstracts Service, Gvinter, L.I. et al., Changes in the Selectivity of Catalytic Action During Hydrogenation of the Dienone Group. IX. Hydrogenation of ?-ionone on Nickel Catalysts, XP002258888, Abstract 83843517 (1975).
Sovoia D et al., Active Metals from Potassium-Graphite. Air-Oxidized Nickel-Graphite as a New Selective Hydrogenation Catalyst, Journal of Organic Chemistry, vol. 46, (1981), pp. 5344-5348, XP009016115.

* cited by examiner

*Primary Examiner*—Michael L. Shippen
(74) *Attorney, Agent, or Firm*—Pendorf & Cutliff

(57) ABSTRACT

A method is described for the preparation of a trimethylcyclohexyl-alkan-3-ol containing a proportion of trans isomer of Formula D

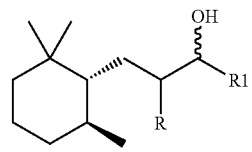

where
R=H, Me, Et, n-propyl, iso-propyl, n-butyl, iso-butyl or tert-butyl and
R1=Me, Et, n-propyl, iso-propyl, n-butyl, iso-butyl or tert-butyl,
or of a mixture of several such trimethylcyclohexyl-alkan-3-ols,
wherein the method comprises catalytically hydrogenating corresponding compound(s) of Formula B

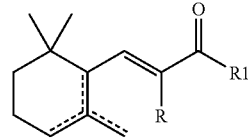

in which R and R1 in each case have the indicated meanings, in the presence of a nickel catalyst, preferably of Raney nickel, and in an absence of catalytically active amounts of copper chromite.

11 Claims, No Drawings

METHOD FOR THE PREPARATION OF TRIMETHYLCYCLOHEXYL-ALKAN-3-OLS CONTAINING A HIGH PROPORTION OF TRANS ISOMERS

CROSS REFERENCE TO RELATED APPLICATIONS

This application claim priority from German Patent Application No. 102 43 466.2-43 filed Sep. 19, 2002.

FIELD OF THE INVENTION

The present invention relates to a method for preparation of a trimethylcyclohexyl-alkan-3-ol of the Formula A

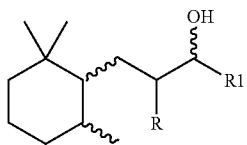

A containing a preferably high proportion of trans isomers of the Formula D

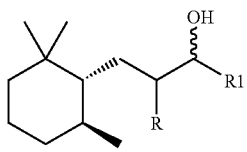

D where

R=H, Me, Et, n-propyl, iso-propyl, n-butyl, iso-butyl or tert-butyl and

R1=Me, Et, n-propyl, iso-propyl, n-butyl, iso-butyl or tert-butyl, or of a mixture of several such trimethylcyclohexyl-alkan-3-ols (which each fall under the Formula A, R and R1 for each mixture constituent being chosen independently of one another and of the other mixture constituents).

DESCRIPTION OF THE RELATED ART

Compounds of the Formula A are valuable odor substances that have found widespread use in the preparation of perfume compositions because of their characteristic woody/ambergris odor as well as the good fixing properties and actions that result because of their structure; cf., for example, DE 24 55 761 A1 and DE 28 07 584 A1.

The trimethylcyclohexyl-alkan-3-ols of the Formula A can be obtained, inter alia, by hydrogenation of the corresponding compounds of the Formula B

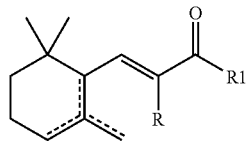

B (in which R and R1 each have the corresponding meaning to that already indicated with regard to Formula D or A).

In this context the broken lines drawn in Formula B represent a single double bond that can be arranged in one of the three positions drawn. Using the nomenclature customary for ionones, this is thus a double bond in an α-, β- or γ-position (cf. Römpp-Lexikon Naturstoffe, Thieme, 1997, page 334–335).

In this context the compounds of the Formula B with triple unsaturation can be prepared in the manner known to those skilled in the art, for example by (a) a condensation reaction of citral with a suitable 2-alkanone and (b) a subsequent cyclisation reaction; cf. for example, Prelog et al. (Helv. Chim. Acta, 31, 417, 1948).

In DE 24 55 761 C2 it is stated that when methyl ionones (compounds of the Formula B with R=Me) are hydrogenated in the presence of Raney nickel as the only catalyst only 12% of the theoretically possible amount of hydrogen are taken up. Thus the hydrogenation does not lead to compounds of the Formula A. According to DE 24 55 761 C2 a hydrogenation does, however, lead to the desired product if it is carried out not in the presence of Raney nickel on its own, but in the simultaneous presence of Raney nickel and copper chromite.

DE 100 62 771 A1 proposes the reduction of 1-(2,2,6-trimethyl-1 or 2-cyclohexen-1-yl)-1-alken-3-ones (compounds of the Formula B) using ruthenium catalysts to give the corresponding 1-(2,2,6-trimethylcyclohexyl)-3-alkanols (compounds of the Formula A) with a high content of trans isomers. However, the hydrogenation proceeds very slowly; in Example 1 of DE 100 62 771 A1 a reaction time of 60 hours is indicated, which would not be acceptable for an industrial process.

It is already known from EP 0 118 809 B1 that the trans isomers of the Formula D are more valuable from the sensory standpoint than the corresponding cis compounds of the Formula C

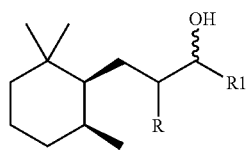

C that are formed on reduction of compounds of the Formula B, always as a mixture with the trans isomers.

In DE 28 07 584 A1 reference is made, without stating the isomer distribution, to 1-(2,6,6-trimethylcyclohexyl)-hexan-3-ol (a compound of the Formula A), which is obtained after total hydrogenation from the corresponding educt compound of the Formula B. The product is marketed by DRAGOCO under the name Timberol and in the later EP 0 118 809 B1 it is stated that Timberol contains no more than 10 to 12% of the trans compound that is more valuable from the sensory standpoint.

In addition to DE 100 62 771 A1, which has already been discussed, a number of other publications also describe the preparation of compounds of the Formula A with as high as possible a proportion of trans isomers of the Formula D. In particular, reference is made to EP 0 118 817 A1 and EP 0 456 932 B1 in this regard. However, the methods described in these publications are not immediately suitable for use on an industrial scale, either because of the use of reagents that are difficult to handle, such as, for example, lithium aluminium hydride, or because of their multi-stage nature.

SUMMARY OF THE INVENTION

The aim of the present invention was, therefore, to develop a method that enables preparation of a trimethylcyclohexyl-alkan-3-ol containing a preferably high proportion of trans isomers of the Formula D or of a mixture of several such compounds in only one reaction step from a simple educt that is obtainable inexpensively.

Preferably, the method to be indicated should be simple and inexpensive to carry out and require only a short reaction time, even on an industrial scale.

Furthermore, preferably no reagents that are difficult to handle should be employed.

Even more preferentially it should be possible for the method to be offered to be set up without high expenditure in such a way that the proportion of trans isomers of the Formula D in the reaction product is at least 15%, based on the total amount of trans and cis isomers prepared.

According to the invention this aim is achieved by a method of the initially mentioned type in which the corresponding compound(s) of the Formula B, in which R and R1 in each case have the meanings indicated initially, is or are catalytically hydrogenated in the presence of a nickel catalyst, preferably of Raney nickel, where (differing in particular from DE 24 55 761 C2) no catalytically active amounts of copper chromite are present.

Amongst the compounds of the Formula B that can be used in the method according to the invention, the following may be mentioned by way of example:

1-(2,6,6-trimethylcyclohex-2-en-1-yl)hex-1-en-3-one

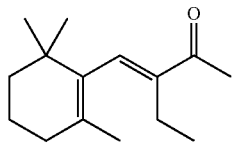

3-ethyl-4-(2,6,6-trimethylcyclohex-1-en-1-yl)but-3-en-2-one

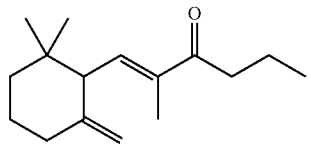

-continued
1-(2,2-dimethyl-6-methylencyclohexyl)-2-methylhex-1-en-3-one

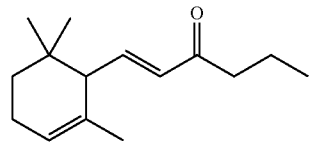

2,4-dimethyl-1-(2,6,6-trimethylcyclohex-1-en-1-yl)pent-1-en-3-one

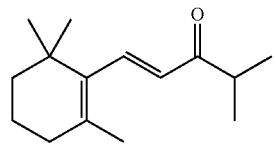

In this context the design of the method according to the invention is essentially independent of whether a mixture of different compounds of the Formula B is used as educt, so that a corresponding mixture of several trimethylcyclohexyl-alkan-3-ols is formed, or only a single compound of Formula B.

Surprisingly, it has been found in extensive studies by the Applicant that the unsuitability of the use of Raney nickel as the sole catalyst that is assumed by those skilled in the art and is documented in particular by the corresponding statements in DE 24 55 761 C2 does not stand up to closer examination. In fact, it is rather the case that complete hydrogenation of compounds of the formula B in the presence of a nickel catalyst is also possible in the absence of catalytically active amounts of copper chromite, the absolute necessity of the presence of which is so vehemently underlined in DE 24 55 761 C2. In this context the nickel catalyst is preferably Raney nickel, with which particularly good yields have been achieved.

Moreover, by variation of individual process parameters it was also possible to determine process conditions suitable for the industrial scale, under which a trimethylcyclohexyl-alkan-3-ol of the Formula A or a mixture of several such trimethylcyclohexyl-alkan-3-ols is prepared with a proportion of at least 15% of trans isomers of the Formula D, based on the total amount of trans and cis isomers prepared. In other words, the following applies for the ratio of the amounts of substance of trans and cis isomers prepared: $n_{trans}/n_{cis} \geq 15:85$. Under particularly preferred conditions it is even the case that: $n_{trans}/n_{cis} > 35:65$.

Particularly good results have been achieved using Raney nickel in an amount of 0.001 to 10% (m/m), preferably 0.1 to 5% (m/m), based on the mass of the compound(s) of the Formula B, in which R and R1 in each case (for each mixture constituent independently of the others) have the indicated meanings, which is used. As has been mentioned, the presence of Cu catalysts is not required.

It was particularly surprising that particularly favorable process results can be achieved if the hydrogenation reaction is carried out in the presence of a base, preferably in the presence of hydroxides, oxides or carbonates of the alkali metals or alkaline earth metals. In particular, it has been found that the presence of bases is able to promote the formation of the trans isomers that are more valuable from the sensory standpoint. In this context the concentration of the base employed should be set depending on its basicity. Thus, for example 1 g NaOH can be replaced by 0.8 g KOH or 2.5 g Ca(OH)$_2$. Depending on the choice of the base used, the use of alkaline aqueous solutions in which the mass ratio of base to water was in the range between 0.1:100 and 50:100 has proved suitable.

In this context the mass ratio of base to catalyst (in particular Raney nickel) used is preferably in the range between 0.01:100 and 10:100, preferably in the range between 1:100 and 3:100.

Preferably, the catalytic hydrogenation is carried out at a temperature in the range between 40 and 350° C., temperatures in the range between 200 and 300° C. having proved particularly advantageous.

The hydrogen pressure during the hydrogenation can be 1–200 bar; a pressure range of 10–50 bar is preferred.

It has proved particularly advantageous to adjust the heating rate of the reaction mixture as a function of the batch size. If the catalytic hydrogenation is to be carried out in the preferred temperature range between 200 and 300° C., the heating rate should be so chosen that the desired reaction temperature—starting from an ambient temperature of approximately 25° C.—is reached within approximately 5 to 60 minutes, but preferably within 10 to 15 minutes. The formation of the trans isomers (Formula D) compared with the formation of the cis isomers (Formula C) is promoted by means of such a measure.

Overall, it is advantageous to carry out the hydrogenation at high temperatures and with short reaction times. A reaction time in the range between 0.5 and 3 hours is preferred. The use of a fixed-bed reactor is advantageous in many cases. This leads not only to a clear rise in the proportion of trans isomers in the product mixture but the space/time yield, which is clearly improved by this means, also leads overall, because of the very short reaction times, to gentle treatment of the product, which, after purification has been carried out, is discernible in an improved sensory quality.

A further process parameter, the optimisation of which can contribute in particular to a shortening of the reaction times, is the stirring speed. Thus, it has been found in experiments that in test autoclaves with gasifying stirrers it was possible by changing the stirring speed under otherwise identical reaction conditions to double the amount of trans isomers of the Formula D formed by increasing from 400 rpm to 1600 rpm. At the same time it was possible to reduce the reaction time from 24 hours to one hour. In general it is the case that an intensive mass transfer favours the formation of the trans isomers. In the case of gasifying stirring, for example, an increase in the speed of revolution leads to a more intense mass transfer, the reason for which is said to be an increased solubility of hydrogen in the reaction medium because of better mixing and better distribution of the heterogeneous catalyst. Installations, such as so-called loop reactors, which promote intense mass transfer between solid, liquid and gas phase also lead to favorable operating conditions and good space/time yields.

It is pointed out that the hydrogenation can take place either in bulk or in solution. Suitable solvents here are in particular alcohols, such as methanol, ethanol, ethylene glycol, propylene glycol and mixtures thereof, esters, such as ethyl acetate, and hydrocarbons such as, for example, hexane and cyclohexane.

It is furthermore pointed out that the use of nickel catalysts, such as Raney nickel, according to the invention not only offers the advantage of yielding reaction products of the Formula A containing a high proportion of trans isomers of the Formula D in a single reaction step starting from the readily accessible compounds of the Formula B, but also effects a more complete conversion of the educt. Finally, the increased conversion leads to a quality of the products that is improved from the sensory standpoint and facilitates their purification.

According to a second aspect, the present invention also relates to a method for the preparation of a perfume composition, with the following steps:
  preparation of a trimethylcyclohexyl-alkan-3-ol containing a high proportion of trans isomers of the Formula D where R=H, Me, Et, n-propyl, iso-propyl, n-butyl, iso-butyl or tert-butyl and R1=Me, Et, n-propyl, iso-propyl, n-butyl, iso-butyl or tert-butyl, or a mixture of several such trimethylcyclohexyl-alkan-3-ols,
  optional isolation and/or purification of the trimethylcyclohexyl-alkan-3-ol or of the mixture,
  mixing of an amount of the trimethylcyclohexyl-alkan-3-ol, or of the mixture, that is effective from the sensory standpoint with one or more conventional perfume constituents.

In this context it is understood that all statements relating to the method according to the invention for the separation of the trimethylcyclohexyl-alkan-3-ol or of the corresponding mixture also apply in this regard.

The invention will be explained in more detail below on the basis of examples.

EXAMPLE 1

2500 g of a mixture of 1-(2,6,6-trimethylcyclohex-1-ene or 2-en-1-yl)-hex-1-en-3-one (80% pure according to GC) with 75 g, corresponding to 3% (m/m), Raney nickel are hydrogenated in a stirred autoclave with a gasifying stirrer under 40 bar hydrogen pressure, at a stirrer speed of 1200 rpm and at a reaction temperature of 280° C.–300° C. for 1 hour. Heating from room temperature up to the reaction temperature takes place in 50 minutes. After filtration and distillation, 1989 g completely hydrogenated product, which contains the 1-(2,2,6-trimethylcyclohexyl)hexan-3-ols in a trans/cis ratio of 1:5, are obtained.

EXAMPLE 2

2500 g of a mixture of methylionone, which contains the n-methylionones 1-(2,6,6-trimethylcyclohex-2-en-1-yl)pent-1-en-3-one (so-called alpha-n-methylionone) and 1-(2,6,6-trimethylcyclohex-1-en-1-yl)pent-1-en-3-one (so-called beta-n-methylionone) in a ratio of approximately 4:1, under 50 bar, with 60 g, corresponding to 2.4% (m/m), Raney nickel and with the addition of 30 g 50% NaOH are hydrogenated in a stirred autoclave with gasifying stirrer at a stirrer speed of 1400 rpm and at a reaction temperature of 2600–280° C. within 1.5 h. Heating from room temperature up to the reaction temperature takes place in 25 minutes. After filtration and distillation, 2290 g completely hydrogenated product, which contains the 1-(2,2,6-trimethylcyclohexyl)pentan-3-ols in a trans/cis ratio of 1:3, are obtained.

EXAMPLE 3

2500 g of a mixture of iso-ethylionone, which contains the iso-ethylionones 1-(2,6,6-trimethylcyclohex-2-en-1-yl)5-methylhex-1-en-3-one and 1-(2,6,6-trimethylcyclohex-1-en-1yl)5-methylhex-1-[lacuna]3-one in a ratio of 3.5:1, with 50 g Raney nickel, 25 g 20% NaOH in water are completely hydrogenated in a stirred autoclave with gasifying stirrer under a hydrogen pressure of 30 bar and at a temperature of 300° C. at 1500 rpm within 45 minutes. Heating from room temperature up to the reaction temperature takes place in 15 minutes. After filtration and distillation, 2350 g completely hydrogenated product, which contains the 5-methyl-1-(2,2,6-trimethylcyclohexyl)hexan-3-ols in a trans/cis ratio of 1:2.1, are obtained.

FURTHER EXAMPLES

The further examples 4 to 20 compiled in the following Table 1 serve for illustration; the parameters from Example 1 are given in the first row of the table. The further examples were carried out in a test autoclave with gasifying stirrer. For the sake of clarity, a mixture as indicated in Example 1 was used in each case.

The base used was 50% sodium hydroxide solution. Experiments with other bases, which have already been described further above, led to comparable results.

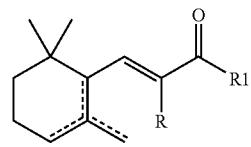

in which R and R1 in each case have the indicated meanings, in the presence of a base and a nickel catalyst, and in an absence of catalytically active amounts of copper chromite.

2. The method according to claim 1, wherein said nickel catalyst is a Raney nickel.

3. The method according to claim 1, wherein process conditions are set such that said trimethylcyclohexyl-alkan-3-ol or said mixture of several such trimethylcyclohexyl-alkan-3-ols contain a proportion of at least 15% trans isomer(s) of Formula C, based on a total amount of trans- and cis isomers prepared.

TABLE 1

| Ex. | Stirrer rpm | Pressure H2 | React. temp. | Heating period | RaNi [%] | Base [g] | Time[1] [min] | trans/cis |
|---|---|---|---|---|---|---|---|---|
| 1 | 1200 | 40 bar | 280–300° C. | 50 min | 3.0 | — | 60 | 1:5.0 |
| 4 | 400 | 30 bar | 180° C. | 60 min | 5.0 | — | 1440 | 1:9.0 |
| 5 | 400 | 30 bar | 180° C. | 60 min | 5.0 | — | 1380 | 1:8.5 |
| 6 | 600 | 30 bar | 180° C. | 60 min | 5.0 | — | 1380 | 1:8.2 |
| 7 | 1200 | 30 bar | 180° C. | 60 min | 5.0 | — | 580 | 1:7.9 |
| 8 | 1200 | 30 bar | 180° C. | 60 min | 5.0 | 5 | 580 | 1:6.8 |
| 9 | 900 | 50 bar | 250° C. | 30 min | 3.0 | 3 | 150 | 1:4.8 |
| 10 | 1400 | 50 bar | 280° C. | 15 min | 2.5 | 5 | 60 | 1:2.9 |
| 11 | 1400 | 50 bar | 280° C. | 15 min | 2.5 | — | 60 | 1:3.5 |
| 12 | 1600 | 20 bar | 300° C. | 15 min | 2.0 | 2 | 45 | 1:2.0 |
| 13 | 1600 | 20 bar | 300° C. | 15 min | 2.0 | — | 45 | 1:2.5 |
| 14 | 1600 | 50 bar | 270° C. | 12 min | 2.0 | 4 | 50 | 1:2.1 |
| 15 | 1600 | 50 bar | 320° C. | 17 min | 1.5 | 3 | 40 | 1:1.8 |
| 16 | 1600 | 50 bar | 320° C. | 17 min | 1.5 | 1 | 40 | 1:2.0 |
| 17 | 900 | 30 bar | 280° C. | 20 min | 0.5 | 1 | 75 | 1:3.4 |
| 18 | 1400 | 10 bar | 330° C. | 10 min | 1.0 | 0.5 | 50 | 1:1.9 |
| 19 | 1400 | 10 bar | 330° C. | 10 min | 2.0 | 0.5 | 50 | 1:1.8 |
| 20 | 1400 | 10 bar | 330° C. | 10 min | 1.0 | — | 50 | 1:2.2 |

[1]Reaction time at reaction temperature.

The invention claimed is:

1. A method for the preparation of a trimethylcyclohexyl-alkan-3-ol containing a proportion of trans isomer of Formula D

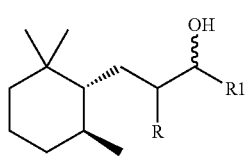

where
R=H, Me, Et, n-propyl, iso-propyl, n-butyl, iso-butyl or tert-butyl and
R1=Me, Et, n-propyl, iso-propyl, n-butyl, iso-butyl or tert-butyl,
or of a mixture of several such trimethylcyclohexyl-alkan-3-ols,
wherein said method comprises catalytically hydrogenating corresponding compounds of Formula B 4. The method according to claim 2, wherein said Raney nickel is used in an amount of 0.001 to 10% (m/m) based on a mass of said compound(s) of Formula B, in which R and R1 in each case have the indicated meanings.

5. The method according to claim 2, wherein said Raney nickel is used in an amount of 0.1 to 3% (m/m) based on the mass of said compound(s) of Formula B, in which R and R1 in each case have the indicated meanings.

6. The method according to claim 1, wherein said base is selected from the group consisting of: hydroxides, oxides, carbonates of alkali metals and carbonates of alkaline earth metals.

7. The method according to claim 1, wherein said catalytic hydrogenation is carried out at a temperature in a range of between 40 and 350° C.

8. The method according to claim 1, wherein said catalytic hydrogenation is carried out at a temperature in the range of between 200 and 300° C.

9. The method according to claim 1, wherein said catalytic hydrogenation is carried out under a pressure in a range of between 1 and 200 bar.

10. The method according to claim 1, wherein said catalytic hydrogenation is carried out under a pressure in the range of between 10 and 50 bar.

11. A method for the preparation of a perfume composition, with the following steps:

preparation of a trimethylcyclohexyl-alkan-3-ol containing a proportion of trans isomers of Formula D

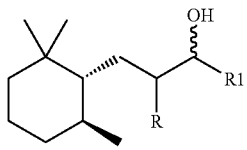

where
R=H, Me, Et, n-propyl, iso-propyl, n-butyl, iso-butyl or tert-butyl and
R1=Me, Et, n-propyl, iso-propyl, n-butyl, iso-butyl or tert-butyl, or of a mixture of several such trimethylcyclohexyl-alkan-3-ols, by a method comprising catalytically hydrogenating corresponding compounds of Formula B

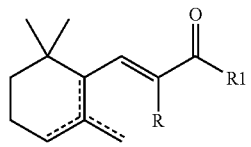

in which R and R1 in each case have the indicated meanings, in the presence of a base and a nickel catalyst, and in an absence of catalytically active amounts of copper chromite, optional isolation and/or purification of said trimethylcyclohexyl-alkan-3-ol or of said mixture, mixing an aroma changing effect amount of said trimethylcyclohexyl-alkan-3-ol or of said mixture with one or more conventional perfume constituents.

* * * * *